United States Patent [19]

Loeffler et al.

[11] 4,262,019
[45] Apr. 14, 1981

[54] THIOPYROCATECHOL DERIVATIVE

[75] Inventors: Hans-Peter Loeffler, Ludwigshafen; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 66,555

[22] Filed: Aug. 15, 1979

[30] Foreign Application Priority Data

Aug. 28, 1978 [DE] Fed. Rep. of Germany ....... 2837406

[51] Int. Cl.³ ................. C07C 125/067; A61K 31/095
[52] U.S. Cl. ................................... 424/300; 560/135
[58] Field of Search ........................ 560/135; 424/300

[56] References Cited

U.S. PATENT DOCUMENTS 3,726,910  4/1973  Reifschneider ..................... 560/135

*Primary Examiner*—Joseph E. Evans
*Attorney, Agent, or Firm*—Keil & Witherspoon

[57] ABSTRACT

The compound 2-(methylthiomethylthio)-phenyl-N-methylcarbamate of the formula

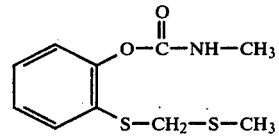

and a process for controlling pests with this compound. The compound is particularly effective on plant-damaging Homoptera.

2 Claims, No Drawings

THIOPYROCATECHOL DERIVATIVE

The present invention relates to the compound 2-(methylthiomethylthio)-phenyl-N-methylcarbamate, pesticides containing 2-(methylthiomethylthio)-phenyl-N-methylcarbamate as active ingredient, and a process for combating pests with this active ingredient.

U.S. Pat. No. 3,726,910 discloses insecticidally effective carbamates of thiopyrocatechol. In addition to other structurally similar compounds, 4-(methylthiomethylthio)-phenyl-N-methylcarbamate, which is suitable for combating flies and ticks, is mentioned.

We have now found that 2-(methylthiomethylthio)-phenyl-N-methylcarbamate of the formula

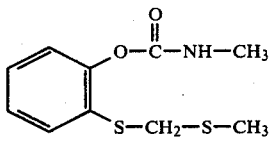

has an excellent action on pests, especially plant pests. The carbamate is superior to prior art thiopyrocatechol carbamates, particularly in its action on Homoptera.

2-(methylthiomethylthio)-phenyl-N-methylcarbamate may be obtained by reaction of 2-(methylthiomethylthio)-phenol with methyl isocyanate, if desired in the presence of a catalyst and, if desired, in the presence of an inert organic solvent.

The reaction is advantageously carried out in an inert organic solvent. Examples of suitable solvents are ethers, such as diethyl ether, dioxane, and tetrahydrofuran, aromatic hydrocarbons, such as benzene, toluene, and xylenes, and chlorinated aliphatic hydrocarbons, such as methylene chloride. Mixtures of these solvents may also be used.

The reaction may if desired be accelerated by catalysts conventionally used for the reaction of isocyanates with phenols, such as organic amines, e.g., trimethylamine, triethylamine, and 1,4-diazabicyclo-[2,2,2]-octane, or organic tin compounds, e.g., di-n-butyltin diacetate and di-n-butyltin dichloride. Advantageously, from 0.0001 to 0.1 mole of catalyst is added per mole of 2-(methylthiomethylthio)-phenol.

Good yields of 2-(methylthiomethylthio)-phenyl-N-methylcarbamate are obtained when the starting materials are used in an equimolar ratio. Generally, from 1 to 2 moles of methyl isocyanate are employed per mole of 2-(methylthiomethylthio)-phenol.

The reaction may be carried out at from −10° to +100° C., and is expediently carried out at from room temperature to 75° C.

The 2-(methylthiomethylthio)-phenol is prepared by reaction of monothiopyrocatechol (J. Chem. Soc., 1514, 1953) with chlorodimethyl sulfide.

The reaction is preferably carried out in solvents and in the presence of equimolar amounts of a base. Solvents which may be used are for example ethers, such as diethyl ether, and dioxane, ketones, such as acetone, and methyl ethyl ketone, and nitriles, such as acetonitrile. Bases which may be employed are for example organic bases, such as triethylamine, or inorganic bases, such as potassium carbonate. It is advisable to carry out the reaction in the absence of oxygen. Monothiopyrocatechol may also be obtained by reaction with formaldehyde in the presence of methyl mercaptan instead of with chlorodimethyl sulfide.

The following example illustrates the preparation of 2-(methylthiomethylthio)-phenyl-N-methylcarbamate.

EXAMPLE

Under a nitrogen blanket, 15.2 g of chlorodimethyl sulfide is dripped into 18.9 g of monothiopyrocatechol in 400 ml of ether. While stirring and at −10° C., 16.7 g of triethylamine is then dripped into this mixture. The whole is stirred for 2 hours at 20° C., the organic phase is washed with water and dried with sodium sulfate, and the solvent is removed. There is obtained 21.5 g of 2-(methylthiomethylthio)-phenol as a weakly colored oil which can directly be further reacted.

3 drops of triethylamine are added to 93 g of 2-(methylthiomethylthio)-phenol in 50 ml of tetrahydrofuran, and 36.8 ml of methyl isocyanate is dripped in while cooling slightly. After the mixture has stood for 12 hours it is concentrated and, with the addition of diethyl ether, is allowed to crystallize. There is obtained 112 g of 2-(methylthiomethylthio)-phenyl-N-methylcarbamate, having a melting point of 85°-86° C.

2-(methylthiomethylthio)-phenyl-N-methylcarbamate is suitable for combating pests, especially from the plant-damaging Homoptera order.

Examples of pests from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Cerosipha forbesi, Sappaphis mali, Sappaphis mala, Dysiphis radicola, Brachycaudus cardui, Brevicoyne brassicae, Phorodon humuli, Rhopalomyzus ascalonicus, Myzus persicae, Myzus cerasi, Dysaulacorthum pseudosolani, Acyrthosiphon onobrychis, Macrosiphon rosae, Macrosiphon solani, Megoura viciae, Schizoneura lanuginosa, Pemphigius bursarius, Dreyfusia nordmannianae, Dreyfusia piceae, Adelges laricis, Viteus vitifolii, Hyalopterus pruni, Phyllaphis fagi, Yezabura tulipae, Eriosoma lanigerum,* and *Eulecanium corni.*

The active ingredient may be applied as such, in the form of formulations, or of read-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient according to the invention.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethyl sulfoxide, N-methylpyrrolidone, and water are suitable.

Aqueous formulations may be prepared from emulsion concentrates, pastes, oil dispersions or wettable powders by adding water. To prepare emulsions, pastes and oil dispersions, the active ingredient as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts or dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredient with a solid carrier.

Granules, e.g., coated, impregnated or homogeneous granules, may be prepared by bonding the active ingredient to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90%, by weight of active ingredient.

The amount of active ingredient in the ready-to-use formulations may vary within a wide range; it is generally from 0.0001 to 10%, preferably from 0.01 to 1%.

The active ingredient may also be successfully used in the ultra-low volume method, where it is possible to apply formulations containing more than 95% of active ingredient, or even the 100% active ingredient.

Examples of formulations are given below.

I. 3 parts by weight of 2-(methylthiomethylthio)-phenyl-N-methylcarbamate is intimately mixed with 97 parts by weight of particulate kaolin. A dust is obtained containing 3% by weight of the active ingredient.

II. 30 parts by weight of 2-(methylthiomethylthio)-phenyl-N-methylcarbamate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of 2-(methylthiomethylthio)-phenyl-N-methylcarbamate is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of caster oil. By pouring the solution into 100,000 parts by weight of water and uniformly distributing it therein, an aqueous dispersion is obtained containing 0.02% by weight of the active ingredient.

IV. 20 parts by weight of 2-(methylthiomethylthio)-phenyl-N-methylcarbanate is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

There may be added to the active ingredient (if desired, immediately before use (tankmix)) oils of various types, herbicides, fungicides, other insecticides, and bactericides. These agents may be added in a weight ratio of from 1:10 to 10:1.

Examples of agents which may be admixed are as follows:

1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, γ-hexachlorocyclohexane, 1,1-di-(p-methoxyphenyl)-2,2,2-trichloroethane, 6,7,8,9,10,10-hexachloro-1,5,5 a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(+)-cis,trans-2,2-dimethyl-3-(2,2-dichlorovinyl)-cyclopropancarboxylate, α-cyano-3-phenoxybenzyl(+)-cis,-trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,-trans-chrysanthemate, 2-methyl-5-(2-propynyl)-3-furyl-methyl-chrysanthemate, and α-cyano-3-phenoxybenzyl-α-isopropyl-4-chlorophenylacetate.

The following examples demonstrate the biological action of the active ingredient according to the invention. The comparative agents employed were 4-(methylthiomethylthio)-phenyl-N-methylcarbamate (1) disclosed in U.S. Pat. No. 3,726,910 and 2-(ethylthiomethyl)-phenyl-N-methylcarbamate (2) disclosed in German Laid-Open Application DE-OS 1,910,588.

EXAMPLE A

Action on bean aphids (Aphid fabae)

Young bean plants (Vicia faba) heavily infected with bean aphid colonies are sprayed to runoff with aqueous formulations of the active ingredients from all sides in a spray cabinet. The action is assessed after 4 days.

| Active ingredient | Concentration % | Kill rate % |
|---|---|---|
| according to invention | 0.002 | 100 |
|  | 0.001 | approx. 80 |
| comparative agent 1 | 0.1 | 50 |
| comparative agent 2 | 0.002 | approx. 80 |

EXAMPLE B

Systemic action on bean aphids (Aphis fabae)

Potted bean plants infected with bean aphids are watered with 30 ml of aqueous formulations of the active ingredients. The action is assessed after 24 hours.

| Active ingredient | Concentration % | Kill rate % |
|---|---|---|
| according to invention | 0.02 | 100 |
|  | 0.01 | approx. 80 |
| comparative agent 1 | 0.1 | ineffective |

We claim:
1. 2-(methylthiomethylthio)-phenyl-N-methylcarbamate of the formula

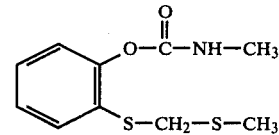

2. A process for selectively combating pests from the Homoptera order, wherein a pesticidally effective amount of 2-(methylthiomethylthio)-phenyl-N-methylcarbamate is allowed to act on the pests or their habitat.

* * * * *